United States Patent [19]

Finger

[11] Patent Number: Plant 6,650

[45] Date of Patent: Mar. 7, 1989

[54] KALANCHOE PLANT NAMED HELIOS

[75] Inventor: Hermann Finger, Wiesmoor, Fed. Rep. of Germany

[73] Assignee: Wiesmoor-Gartnerie und Baumschule GmbH, Wiesmoor, Fed. Rep. of Germany

[21] Appl. No.: 108,985

[22] Filed: Oct. 16, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Kalanchoe plant named Helios, having bright yellow flowers, good basal branching, dense and large flower head, highly floriferous habit, vigorous upright growth, and excellent keeping quality.

1 Drawing Sheet

1

The present invention relates to a new and distinctive cultivar of Kalanchoe plant, botanically known as *Kalanchoe blossfeldiana,* and known by the cultivar name Helios. Helios was developed by me through controlled breeding in Wiesmoor, Federal respublic of Germany by crossing Fortyniner (U.S. Plant Pat. No. 5,256), the seed parent, with Inspiration (U.S. Plant Pat. No. 5,899), the pollen parent.

Asexual reproduction by me in Wiesmoor, Federal Republic of Germany by stem cuttings of Helios of a selection from the progeny of the stated cross has shown that the unique features of this new Kalanchoe are stabilized and are reproduced true to type in successive propagations.

The following characteristics distinguish the new Kalanchoe from both its parent varieties and other cultivated Kalanchoes of this type known and used in the floriculture industry:

1. Helios is characterized by its bright yellow fowers, as compared to Fortyniner (U.S. Plant Pat. No. 5,256), which has lighter yellow flowers, Firefly (U.S. Plant Pat. No. 4,728), a deeper duller yellow, and Goldstrike, a golden yellow. Goldstrike is disclosed in a pending application.

2. Helios is similar in maturity to Goldstrike and one week earlier than Firefly and Fortyniner.

3. Helios is similar in height to Firefly, with Fortyniner and Goldstrike being more compact.

4. Basal branching of Helios is superior to Firefly and similar to Goldstrike and Fortyniner.

5. Flower size of Helios is similar to Goldstrike, and slightly smaller in size, although more numerous in flowers than either Fortyniner or Firefly.

6. Flower cluster of Helios is dense and large, with a large number of branches in the head, similar to Goldstrike. Both Fortyniner and Firefly have a more open cluster with less branching.

7. Leaf size of Helios is smaller than Firefly, similar to Goldstrike but larger than Fortyniner.

8. Helios has a yellow green leaf which is similar in color to Firefly and Goldstrike, with Fortyniner having a darker green leaf.

9. The leaf margins are crenate with a shallow cut similar to Firefly and Fortyniner, with Helios having a deeper cut margin.

10. Helios has excellent keeping quality under high light and temperatures, comparable to Goldstrike. Firefly has inferior keeping quality.

2

The accompanyng colored photograph illustrates in top perspective view the overall appearance of Helios, with colors being as true as it is reasonably possible to obtain in a colored reproduction of this type.

The following is a detailed description of my new kalanchoe variety based on plants produced under commercial practices in Wiesmoor, Federal Republic of Germany and Ashtabula, Ohio. Color references are made to The Royal Horticultural Society Colour Chart, except where general colors of ordinary dictionary significance are used.

Parentage: A controlled cross between the female parent Fortyniner and the male parent Inspiration.

Propagation:

(A) *Type cutting.*—2 cm tip cuttings.

(B) *Time to root.*—10 days at 21° C. summer. 14 days at 21° C. winter.

(C) *Rooting habit.*—Abundant; fine, fibrous roots.

Plant description:

(A) *Form.*—Semi-compact, upright growth habit; carries flowers above foliage; excellent basal branching for a yellow cultivar. Growing and scheduling practices can produce a small plant in a 10 cm pot or a larger plant in a 12 cm pot.

(B) *Habit of growth.*—Vigorous grower with shoots forming at every node. Due to the upright growth habit flower head is at top of plant, with the bottom of the plant being somewhat open.

(C) *Foliage.*—Leaves simple, opposite. (1) Size: A full grown leaf of a flowering plant in a 10 cm pot is 100 mm long and 70 mm wide. (2) Shape: Ovate, apex obtuse, base acute. (3) Texture: Glabrous, succulent, coriaceous. (4) Margin: Pronounced crenate to dentate. (5) Color: Young foliage, top side 137A, under side 137C. Mature foliage, top side 137B, under side 147B.

Flowering description:

(A) *Flowering habits.*—Inflorescence is a cyme with the terminal flower of the main axis opening first, followed by terminal flowers of the side branches, continuing with subsequent development of branches in the inflorescence.

(B) *Natural flowering season.*—Early January. Flowering time under controlled daylength at 20° C. in summer is 10 weeks; in winter 12 weeks. Flowering time depends on temperature, light intensity and other growing conditions.

(C) *Flower buds.*—Elliptical to oblong, up to 10 mm long, developing to tubular as flower petals mature, sheathed with four green sepals; corolla in maturity is 7 mm long.

(D) *Flowers borne.*—On compound dichisial cymes, primary peduncle 4 mm in diameter, with peduncle length depending on environment and B-9 application. Pedicles are up to 5 mm long.

(E) *Quantity of flowers.*—Highly floriferous, main stem has over 100 flowers with 6 or more side branches having 40 or more flowers.

(F) *Petals.*—(1) Shape: Almost round, top cuspidate. (2) Color: Top side, when opening, 13B; under side 13C. (3) Number of petals: 4.

(G) *Reproductive organs.*—(1) Stamens: Eight (8) in number. (a) Anther shape: Flat, elliptical, color yellow. (b) Filament color: Light green. (c) Pollen color: Yellow. (2) Pistils: (a) Stigma shape: Flat, color light green. (b) Style color: Light green. (c) Ovaries: 4 in number, size 5 mm, color light green.

Disease resistance: No disease problems observed to date.

Other important characteristics: Shows good resistance to heat delay of flower buds under short day treatment under blackcloth during periods of high temperatures. Bright yellow flowers retain an attractive color as they age.

I claim:

1. A new and distinct cultivar of Kalanchoe plant named Helios, as illustrated and described.

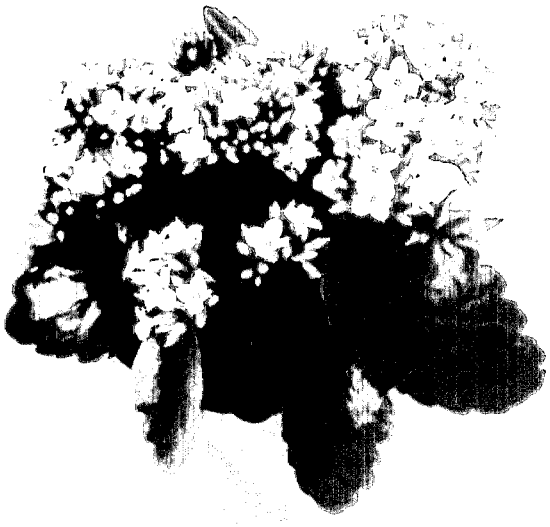

* * * * *